United States Patent [19]
Schmidt et al.

[11] Patent Number: 5,977,329
[45] Date of Patent: Nov. 2, 1999

[54] METHODS OF SYNTHESIZING GM3

[75] Inventors: Richard Schmidt; Julio C. Castro-Palomino, both of Constance, Germany; Gerd Ritter; Lloyd J. Old, both of New York, N.Y.

[73] Assignee: Ludwig Institute for Cancer Research, New York, N.Y.

[21] Appl. No.: 09/024,528

[22] Filed: Feb. 17, 1998

Related U.S. Application Data

[63] Continuation-in-part of application No. 08/602,580, Feb. 16, 1996, Pat. No. 5,756,695.

[51] Int. Cl.⁶ .................................................. C07H 15/00
[52] U.S. Cl. ........................................ 536/18.6; 536/18.5
[58] Field of Search .................................. 536/18.5, 18.6

[56] References Cited

U.S. PATENT DOCUMENTS

| 4,593,091 | 6/1986 | della Valle et al. ..................... 536/53 |
| 5,756,695 | 5/1998 | Schmidt et al. ......................... 536/18.5 |

OTHER PUBLICATIONS

Sugimoto et al. *Carbohydr. Res.* 1986, 156, C1–C5. Month not available.

Hasegawa et al., "Synthetic Studies on Sialoglycoconjugates 41: A Facile Total Synthesis of Ganglioside $GM_2$," *J. Carbohydrate Chem.* 11(6):669–714, 1992 (month not available).

Schmidt, "Chemical Synthetis of Sialylated Glycoconjugates in Synthetic Oligosaccharides: Indispensable Probes for the Life Sciences," (*ACS Syposium Genes*, 560, 1994) (month not available).

Martin et al., "Synthesis of Phosphites and Phosphates of Neuraminic Acid and Their Glycosyl Donor Properties—Convenient Synthesis of $GM_2$," *Glycoconjugate Journal*, 10:16–25 (1993) (month not available).

*Primary Examiner*—Kathleen K. Fonda
*Attorney, Agent, or Firm*—Fulbright & Jaworski, LLP

[57] ABSTRACT

The invention describes an improved method for making monosialoganglioside GM3 and its intermediates. Following reaction of a neuraminic acid donor and a lactose acceptor in the presence of an acid catalyst, the α and β isomers of GM3 are formed. The α isomer is converted to a lactone, via action of a ring forming basic catalyst, which is then separable from the β isomer. The lactone is then treated with a basic catalyst in the presence of an alcohol, to form GM3 or a GM3 intermediate.

12 Claims, No Drawings

METHODS OF SYNTHESIZING GM3

RELATED APPLICATIONS

This application is a continuation-in-part of Ser. No. 08/602,580, filed Feb. 16, 1996 now U.S. Pat. No. 5,756,695, and incorporated by reference.

FIELD OF THE INVENTION

This invention relates to methods of producing synthetic GM3s. The compounds produced by the methods of the invention are useful in the same way all of the gangliosides are, and can also be used as a starting material for additional synthetic reactions.

BACKGROUND OF THE INVENTION

Gangliosides are a class of molecules which are glycolipids. Different gangliosides have been identified as prominent cell surface constituents of various transformed cells, including melanoma, as well as other tumors of neuroectodermal origin. See, e.g., Ritter and Livingston, et al., *Sem. Canc. Biol.*, 2:401–409 (1991) and Oettgen, VCH Verlags Gesellschaft (Weinheim Germany 1989), both of which are incorporated herein by reference.

Gangliosides are known as mono-, di-, tri or polysialogangliosides, depending upon the degree of glycosylation with sialic acid residues. Abbreviations employed to identify these molecules include "GM1", "GD3", "GT1", etc., with the "G" standing for ganglioside, "M", "D" or "T", etc. referring to the number of sialic acid residues, and the number or number plus letter (e.g., "GT1a"), referring to the binding pattern observed for the molecule. See Lehninger, *Biochemistry*, pg. 294–296 (Worth Publishers, 1981); Wiegandt, *Glycolipids: New Comprehensive Biochemistry* (Neuberger et al., ed., Elsevier, 1985), pp. 199–260.

The monosialoganglioside GM3 has the structure:

2αNeuAc→3Galβ1→4GKβ1-ceramide

The gangliosides are prevalent cell surface markers on transformed cells, such as melanoma. This has made them attractive targets for cancer research. Livingston, et al., *Proc. Natl. Acad. Sci. USA*, 84:2911–2915 (1987), which is incorporated herein by reference, describe results of a vaccine based trial, wherein subjects afflicted with melanoma received, as vaccines, either whole cells which present high levels of GM2, pure GM2 or pure GM2 plus bacterial adjuvant. Attention is drawn to Livingston, et al., *J. Clin. Oncol.*, 12(5):1036–1044 (1994), and Irie, et al., U.S. Pat. No. 4,557,931, both of which are incorporated herein by reference, and deal with the use of GM2 as a vaccine.

There are difficulties unique to the immunology of gangliosides, which are touched upon briefly here. First, while these molecules are prevalent on transformed cells, they are also common on certain normal cells, such as neural cells. There is a risk, in administering gangliosides to a subject, that the resulting antibody response will damage normal cells. Indeed, certain autoimmune pathologies, such as Guillain-Barre' Syndrome, are characterized by autoimmune antibodies reactive with GM1 or GQ1b. See, e.g., Yuki, et al., *J. Exp. Med.*, 178:11771–1775 (1993); Aspinall, et al., *Infect & Immun.*, 62(5):2122–2125 (1994).

There is an additional practical problem in that highly pure gangliosides are extremely difficult to secure in amounts sufficient for immunization protocols. No practical synthetic method is presently available. As a result, gangliosides are secured via purification from tissue, such as bovine cranial tissues. Even under optimum conditions, the yields of pure gangliosides, including GM2 and GM3, are vanishingly small. Further, purification from mammalian tissue carries with it the risk of transmitting contaminants such as viruses, prion particles, and so forth. Alternate methodologies for securing ganglioside specific antibodies are thus highly desirable.

Due to the importance of gangliosides, it is desirable to develop a method of synthesizing high yields of pure gangliosides. The inventors of the instant application have developed novel methods of synthesizing pure GM2s, in high yields. Other methods of developing synthetic GM2s are described in Hasegawa et al., *J. Carbohydrate Chemistry*, 11(6):699–714 (1992) and Sugimoto et al., *Carbohydrate Research*, 156:C1–C5 (1986). The invention described herein develops the art in that the methods described herein are not suggested by these references.

Synthesis of GM2 can be expedited if GM3 is used as a starting material; however, GM3 is difficult to obtain from the source materials described supra, for all of the reasons given. Hence, it is desirable to have a process available which facilitates large scale production of GM3, which is free of the problems set forth supra. The invention relates, inter alia, to a process which meets these goals.

SUMMARY OF THE INVENTION

The invention relates to a process for synthesizing GM3, and GM3 intermediates, which results in quick production of large amounts of the desired product. In one embodiment of this process, a neuraminic acid donor, is reacted with a lactose acceptor. This reaction, when carried out in the presence of an acid catalyst, yields a GM3 intermediate, as is detailed, infra, and a β-isomer of GM3. The β-isomer is an undesired product of the reaction; however, it is difficult to separate the desired GM3 intermediate and the β-isomer quickly and efficiently. It has now been found, however, that by reacting the desired GM3 intermediate in the presence of a basic catalyst, a lactone compound is formed, which is easily separated from the β-isomer. In turn, the lactone can be reacted with a combination of the basic catalyst and an alcohol, to form the- desired GM3 or GM3 intermediate. As a result, GM3 and its intermediates can be produced quickly, and in gram quantities.

How this is accomplished will be seen in example 1 et seq., which follow.

In the instant invention, acidic catalysts are used to react neuraminic acid donors and lactose donors to form GM3 intermediates. Specifically, to form the desired compounds, one reacts, e.g.

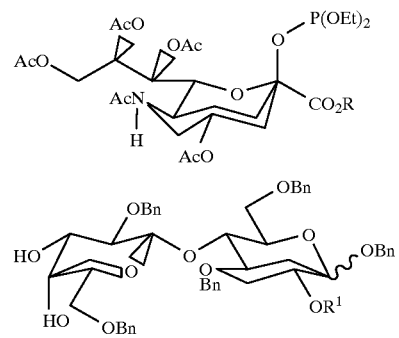

wherein R is C1–C6 straight chained or branched alkyl, phenyl, or benzyl, optionally substituted at least once with a group containing oxygen, nitrogen, or sulfur. Preferably, R is C1–C6 alkyl. Most preferably, it is straight chained methyl, ethyl, propyl or butyl. $R^1$ is benzyl, benzoyl, pivaloyl or acetyl.

As indicated supra, this reaction riot only forms GM3 or GM3 intermediates also forms β isomers, i.e.:

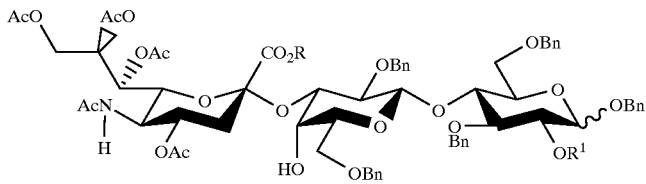

and

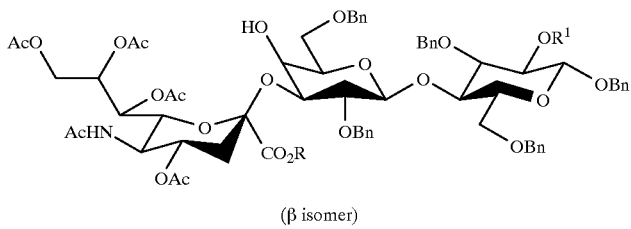

(β isomer)

wherein R is as described, supra. These two classes of compounds, i.e., the desired compounds and the β isomer, are not easily separable. One can do so, however, by adding a basic catalyst, which is exemplifiedby 1,8-diazabicyclo (5.4.0)undec-7-ene ("DBU" hereafter), triethylamine, or other similar compounds. These compounds are catalytic in that they facilitate formation and closing of lactone rings, in the desired product when used alone, but opening of fused rings, when used with an alcohol.

Following formation of the lactone, which can be depicted as:

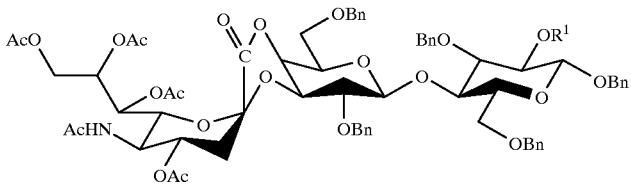

One easily separates the lactone from the β-isomer. The lactone is then reacted, again with a basic catalyst in the presence of an alcohol of formula ROH, where R may contain from 1 to 10, preferably 1 to 6 carbon atoms, such as methyl or benzyl alcohols. In the presence of such an alcohol, the lactone ring opens, to form a GM3 intermediate, depending upon the alcohol used.

Example 2, which follows, sets this forth. If the lactone is available as a source material, of course one does not have to make it, and can simply proceed with the addition of the basic catalyst and alcohol.

EXAMPLE 1

In order to prepare $II^3NeuAcGgOse_3Cer$, referred to herein as GM3, I, a neuraminic acid donor and compounds II, lactose acceptors, were prepared as described by T. J. Martin et al., *Glycoconiugate J.* 1993, supra. In order to obtain compounds III, i.e., GM3, a solution of neuraminic acid donor (1 mmol) and lactose acceptors (1.5 mmol) in dry acetonitrile (5 mL) was cooled to −40° C. Under a nitrogen atmosphere the catalyst (0.15 mmol) tin(II) trifluoromethanesulfonate) was added. After 1 hour, the solution was neutralized with triethylamine and evaporated in vacuo. The residue was purified by flash chromatography on silica gel with toluene-acetone (3:1) as eluent to give compound III in 65% yield. For NMR data, see T. J. Martin et al., *Glycoconjugate J.* 1993, supra.

EXAMPLE 2

Example 1 sets forth a procedure which is useful in making milligram quantities of GM3. If large scale production of GM3 (i.e., gram quantities) is desired, a better method is necessary. Such a method follows. In these methods, the same compounds as were used in example 1 were combined. In the structures which follow $R^1$ may be benzyl, benzoyl, acetyl, pivaloyl, and so forth. The compounds are combined, in the presence of Sn(II) trifluoromethane sulfonate, an acid catalyst of the type described supra. The products of this reaction are a GM3 intermediate, and a β isomer of GM3, i.e.:

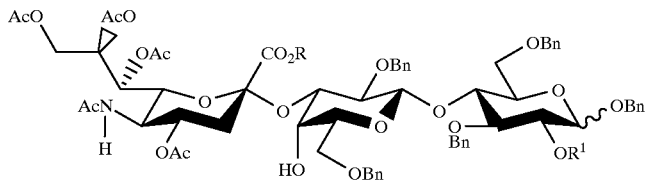

and

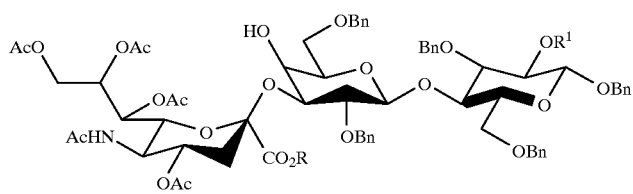

The basic catalyst 1,8-diazabicyclo(5.4.0)undec-7-ene was then added, to form the lactone:

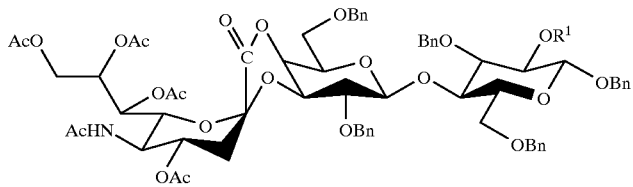

It is very easy to separate the lact/one of GM3 from the β isomer of GM3 whereas it is very difficult to separate the α and α isomers.

Once the lactone is separated from the GM3, the lactone is treated with an alcohol, such as methyl alcohol and 1,8-diazabicyclo (5.4.0) undec-7-ene, to yield the desired GM3 intermediate.

Specifics of this process follow.

EXAMPLE 3

A solution of the lactose acceptor, supra, where $R^1$ is pivaloyl (200 mg, 0.23 mmol), and Sn(II) trifluoromethane sulfonate (25 mg, 0.06 mmol), in dry acetonitrile was cooled to −40° C. A solution of the neuraminic acid donor (183 mg, 0.30 mmol), in dry acetonitrile, supra was dropwise added to this first solution, under a nitrogen atmosphere. This yielded the desired GM3, and the β isomer depicted supra.

One hour after the two solutions were combined, 90 ul (0.60 mmol) of 1,8-diazabicyclo(5.4.0)undec-7-ene was added, and the resulting solution was stirred, for one hour, at room temperature.

The solution was then neutralized with ion exchange resin, filtered, and evaporated in vacuo, and the residue was purified by column chromatography. A fast migrating spot, corresponding to the GM3-lactone depicted supra was found, in 60% yield (186 mg) while a lower migrating spot, corresponding to β-GM3 as depicted supra was also found, in 6% yield (21 mg). The lactone was examined for NMR properties, which confirmed that it was, in fact the desired lactone.

The lactone was separated from the column, and put into a solution of dry methanol (200 mg, 0.17 mmol of lactone; 5 ml of methanol), cooled to −20° C. and then less than 1 ul of 1,8-diaza-bicyclo(5.4.0)undec-7-ene was added. The solution was stirred for two hours at −20° C. Thereafter, the solution was neutralized with acetic acid, and evaporated. Column chromatograph yielded 144 mg, or 70% of the desired GM3 intermediate as a product.

This procedure, as indicated supra, resulted in production of a GM3 lactone, which is easily separated from the β-isomer of GM3, and can then be used to produce the desired GM3 intermediate. A time period of about ½ a day is necessary to yield a gram quantity of GM3, as compared to about one week, using the former procedure.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A process for preparing a compound of formula I:

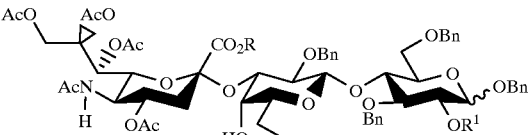

comprising combining a compound of formula II:

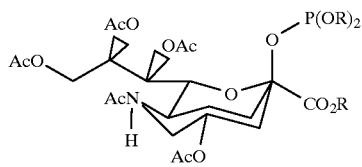

wherein R in each case is C1–C6 straight chained or branched alkyl, phenyl or benzyl, optionally substituted at least once by an oxygen, nitrogen, or sulfur containing group, with a compound of formula III:

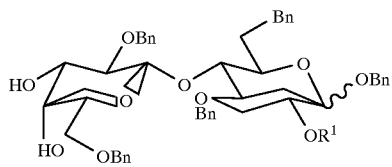

wherein $R^1$ is benzyl, benzoyl, acetyl or pivaloyl, to form a mixture of

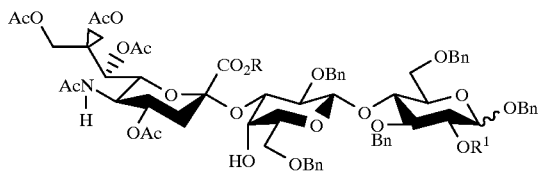

and β isomer:

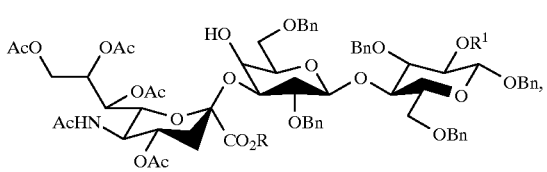

adding a basic catalyst to said mixture to form a lactone of formula:

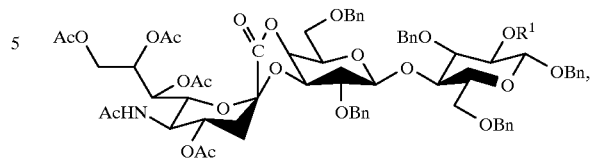

separating said lactone from said β isomer, and reacting said lactone with a basic catalyst and an alcohol, to form said compound of formula I.

2. The process of claim 1, wherein said alcohol is methyl alcohol or benzyl alcohol.

3. The process of claim 2, wherein said alcohol is methyl alcohol.

4. The process of claim 1, wherein said acid catalyst is tin(II) trifluoromethane sulfonate.

5. The process of claim 1, wherein said basic catalyst is 1,8-diazabicyclo (5.4.0) undec-7-ene, or triethylamine.

6. The process of claim 5, wherein said basic catalyst is 1,8-diazabicyclo (5.4.0) undec-7-ene.

7. The process of claim 1, further comprising separating said lactone from said β isomer via column chromatography.

8. A process for making a compound of formula I:

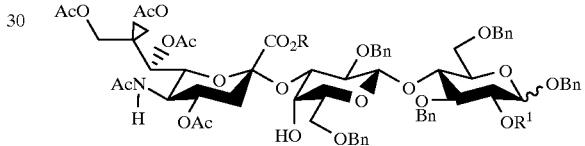

wherein $R^1$ is benzyl, benzoyl, pivaloyl or acetyl comprising reacting a compound of formula II,

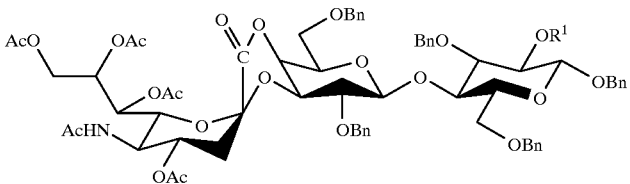

wherein $R^1$ is benzyl, benzoyl, pivaloyl or acetyl, with a basic catalyst and an alcohol to form a compound of formula I.

9. The process of claim 8, wherein said alcohol is methyl alcohol or benzyl alcohol.

10. The process of claim 9, wherein said alcohol is methyl alcohol.

11. The process of claim 8, wherein said basic catalyst is 1,8-diazabicyclo (5.4.0) undec-7-ene or triethylamine.

12. The process of claim 8, wherein said basic catalyst is 1,8-diazabicyclo (5.4.0) undec-7-ene.

* * * * *

UNITED STATES PATENT AND TRADEMARK OFFICE
CERTIFICATE OF CORRECTION

PATENT NO. : 5,977,329
DATED : Nov. 2, 1999
INVENTOR(S) : Schmidt et al.

It is certified that error appears in the above-indentified patent and that said Letters Patent is hereby corrected as shown below:

On cover page, in the section entitled Other Publications, on the line regarding Schmidt, change "1994" to -- 1993 --.
In column 3, line 24, change "exemplifiedby" to -- exemplified by --.
In column 5, line 33, change "lact/one" to -- lactone --.

Signed and Sealed this

Eighth Day of May, 2001

Attest:

NICHOLAS P. GODICI

Attesting Officer

Acting Director of the United States Patent and Trademark Office